US008632244B2

(12) United States Patent
Bar-Cohen et al.

(10) Patent No.: US 8,632,244 B2
(45) Date of Patent: Jan. 21, 2014

(54) IN-SERVICE MONITORING OF STEAM PIPE SYSTEMS AT HIGH TEMPERATURES

(75) Inventors: Yoseph Bar-Cohen, Seal Beach, CA (US); Shyh-Shiuh Lih, Porter Ranch, CA (US); Mircea Badescu, La Canada Flintridge, CA (US); Xiaoqi Bao, San Gabriel, CA (US); Stewart Sherrit, La Crescenta, CA (US); James Samson Scott, Torrance, CA (US); Julian O. Blosiu, San Marino, CA (US); Scott E. Widholm, La Crescenta, CA (US)

(73) Assignee: California Institute of Technology, Pasadena, CA (US)

( * ) Notice: Subject to any disclaimer, the term of this patent is extended or adjusted under 35 U.S.C. 154(b) by 3 days.

(21) Appl. No.: 13/043,499

(22) Filed: Mar. 9, 2011

(65) Prior Publication Data
US 2011/0222577 A1 Sep. 15, 2011

Related U.S. Application Data

(60) Provisional application No. 61/312,164, filed on Mar. 9, 2010.

(51) Int. Cl.
*G01K 13/02* (2006.01)
(52) U.S. Cl.
USPC ........................................................ 374/117
(58) Field of Classification Search
USPC .......... 73/602, 865.5, 19.03, 628, 599, 61.75, 73/24.02, 24.03, 61.41, 61.42, 596; 310/337, 341, 311, 73
See application file for complete search history.

(56) References Cited

U.S. PATENT DOCUMENTS

| 6,212,943 | B1* | 4/2001 | Maltby et al. ................. 73/61.49 |
| 6,279,379 | B1* | 8/2001 | Logue et al. ................. 73/24.01 |
| 6,988,026 | B2* | 1/2006 | Breed et al. ................. 701/31.4 |
| 7,079,450 | B2* | 7/2006 | Breed et al. ................. 367/138 |
| 7,140,239 | B2* | 11/2006 | Greenwood et al. ......... 73/61.63 |
| 7,184,930 | B2* | 2/2007 | Miyasaka et al. ............. 702/183 |
| 7,253,742 | B2* | 8/2007 | Davis et al. ................. 340/606 |
| 7,331,233 | B2* | 2/2008 | Scott ............................ 73/596 |

(Continued)

OTHER PUBLICATIONS

"Compact-RIO—Programmable Automation Controller", National Instruments, wayback capture, Dec. 29, 2007.*

(Continued)

*Primary Examiner* — Lisa Caputo
*Assistant Examiner* — Nasir U Ahmed
(74) *Attorney, Agent, or Firm* — Milstein Zhang & Wu LLC; Joseph B. Milstein

(57) ABSTRACT

A system and method for monitoring the properties of a fluid, such as water, in a steam pipe without mechanically penetrating the wall of the pipe. The system uses a piezoelectric transducer to launch an ultrasonic probe signal into the pipe. Reflected ultrasonic signals are captured in a transducer, which can be the same transducer that launched the probe signal. The reflected signals are subjected to data processing, which can include filtering, amplification, analog-to-digital conversion and autocorrelation analysis. A result is extracted which is indicative of a property of the fluid, such as a height of the condensed fluid, a cavitation of the condensed fluid, and a surface perturbation of the condensed fluid. The result can be recorded, displayed, and/or transmitted to another location. One embodiment of the system has been constructed and tested based on a general purpose programmable computer using instructions recorded in machine-readable non-volatile memory.

15 Claims, 20 Drawing Sheets

(56) References Cited

U.S. PATENT DOCUMENTS

| | | | |
|---|---|---|---|
| 7,360,403 B2* | 4/2008 | Jones et al. | 73/61.75 |
| 2002/0120422 A1* | 8/2002 | Nagase | 702/127 |
| 2003/0051886 A1* | 3/2003 | Adiga et al. | 169/43 |
| 2004/0000877 A1* | 1/2004 | Morton et al. | 315/169.3 |
| 2004/0016284 A1* | 1/2004 | Gysling et al. | 73/1.16 |
| 2004/0168522 A1 | 9/2004 | Fernald et al. | |
| 2005/0011258 A1* | 1/2005 | Gysling et al. | 73/195 |
| 2005/0050956 A1 | 3/2005 | Gysling et al. | |
| 2005/0140212 A1* | 6/2005 | Hamel et al. | 307/44 |
| 2006/0144148 A1 | 7/2006 | Gysling et al. | |
| 2007/0083340 A1* | 4/2007 | Bailey et al. | 702/100 |
| 2008/0018199 A1* | 1/2008 | Trolier-McKinstry et al. | 310/311 |

OTHER PUBLICATIONS

"NI CRIO-9072—Integrated Real-Time Controller", National Instruments, wayback capture, Jan. 24, 2008.*

WO 2011/112641 A3, International Search Report for Corresponding PCT application, PCT/US2011/027628, dated Sep. 15, 2011 (5 pages).

* cited by examiner

| FIG. 6A | FIG. 6B | FIG.6C |

Reflection signals from the bonded coupon shows no ringing between the plates.

IN-SERVICE MONITORING OF STEAM PIPE SYSTEMS AT HIGH TEMPERATURES

CROSS-REFERENCE TO RELATED APPLICATIONS

This application claims priority to and the benefit of U.S. provisional patent application Ser. No. 61/312,164 filed Mar. 9, 2010, which application is incorporated herein by reference in its entirety.

STATEMENT REGARDING FEDERALLY FUNDED RESEARCH OF DEVELOPMENT

The invention described herein was made in the performance of work under a NASA contract, and is subject to the provisions of Public Law 96-517 (35 USC 202) in which the Contractor has elected to retain title.

FIELD OF THE INVENTION

The invention relates to systems and methods for measuring the contents of piping systems in general and particularly to systems and methods that operate at high temperature and high pressure.

BACKGROUND OF THE INVENTION

Generally, steam pipes are used as part of a district heating system in many cities carrying steam from central power stations under the streets to heat, cool, or supply power to high rise buildings and businesses. Some businesses and facilities also use the delivered steam for cleaning and sterilization. In addition to providing space and water heating, the steam is used in numerous restaurants for food preparation, laundries and dry cleaners, as well as to power absorption chiller systems for air conditioning. The New York Steam Company began providing this service in lower Manhattan in 1882. Today, Con Edison operates this system that has grown to become the largest commercial steam system in the world. Con Edison now transmits about 14 million tons per year of steam through its pipe system. The steam flows at a relatively high speed and it can reach over 100 miles per hour. It is common to see the emission of vapors from manholes in Manhattan and it mostly caused by external water being boiled resulting from contact with a steam pipe and it does not necessarily represent a leak in the steam system.

One of the concerns to such a system is the excitation of water hammer that may lead to serious consequences including damaged vents, traps, regulators and piping. The water hammer is caused by accumulation of condensed water that is trapped in a portion of horizontal steam pipes. The velocity of the steam flowing over the condensed water causes ripples in the water creating buildup of turbulence and resulting in the water formation of a solid mass or slug that fills the pipe. The slug of the condensed water can travel at the speed of the steam striking the first elbow that is encountered in its path. The force can be comparable to a hammer blow and can be sufficiently large to break the back surface of the elbow.

There is a need for systems and methods that can provide real time monitoring of pipes that operate at high temperature and elevated pressure.

SUMMARY OF THE INVENTION

According to one aspect, the invention features a steam pipe monitoring system. The steam pipe monitoring system comprises a piezoelectric transducer configured to be operable at a temperature present at an external surface of a steam pipe to be monitored, the piezoelectric transducer configured to be bonded to the external surface of the steam pipe, the piezoelectric transducer configured to emit a probe ultrasonic signal in response to a received activation signal, and configured to receive a reflected ultrasonic signal and to provide an electrical signal representative of the reflected ultrasonic signal; a signal generator configured to provide the activation signal to the piezoelectric transducer; an amplifier configured to receive the electrical signal representative of the reflected ultrasonic signal from the piezoelectric transducer, configured to amplify the electrical signal, and configured to provide as output an amplified electrical signal; a signal processing module comprising an analog-to-digital converter, a digital signal processor, and a transceiver, the signal processing module configured to receive the amplified electrical signal, configured to process the amplified electrical signal to extract data indicative of a property of a fluid present in the steam pipe, and configured to transmit information about the property of the fluid for use by a user; and a power supply configured to provide power to operate the piezoelectric transducer, the signal generator, the amplifier and the signal processing module.

In one embodiment, the signal processing module is additionally configured to receive a command signal by way of the transceiver, the command signal configured to control an operation of the steam pipe monitoring system.

In another embodiment, the temperature present at an external surface of a steam pipe to be monitored is a temperature from ambient temperature up to 250° C.

In yet another embodiment, the signal processing module comprises a general purpose programmable computer based system using instructions recorded in machine-readable non-volatile memory.

In still another embodiment, the property of the fluid is a height of the fluid.

In a further embodiment, the property of the fluid is a perturbation of the fluid.

In yet a further embodiment, the perturbation of the fluid is selected one of a cavitation of the fluid and a perturbation of a surface of the fluid.

In one more embodiment, the fluid present in the steam pipe is water.

In another embodiment, the piezoelectric transducer configured to be bonded to the external surface of the steam pipe is additionally mechanically connected to the external surface of the steam pipe.

According to another aspect, the invention relates to a method of monitoring a property of a fluid in a steam pipe. The method of monitoring a property of a fluid in a steam pipe comprises the steps of providing a probe ultrasonic signal at an external surface of a steam pipe; receiving reflected ultrasonic signals at the external surface of the steam pipe, the reflected ultrasonic signals present in response to the probe ultrasonic signal; processing the reflected ultrasonic signals to deduce a property of a fluid in the steam pipe; providing an electrical signal indicative of the property of the fluid in the steam pipe as a result; and performing at least one of recording the result, transmitting the result to a data handling system, or to displaying the result to a user.

In one embodiment, the step of processing the reflected ultrasonic signals comprises filtering the reflected ultrasonic signals.

In another embodiment, the step of processing the reflected ultrasonic signals comprises applying an autocorrelation procedure to extract data.

In yet another embodiment, the step of processing the reflected ultrasonic signals is performed using a data-logging program.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Herein disclosed is a steam pipe health monitoring system that operates in-service to track at high temperatures through a wall in real-time the height of condensed water. The system accounts for the effects of water flow and cavitation. For this purpose, ultrasonic waves were used to perform data acquisition of reflected signals in pulse-echo and via autocorrelation the data was processed to determine the water height. Transmitting and receiving the waves is done by a high temperature piezoelectric transducer that has a high Curie temperature above the expected temperature range.

It is believed that the novel features of this disclosure include:

A system that monitors the height of water condensation in steam pipes through the wall of the pipe.

A water condensation height measurement system that performs in conditions of height disturbances and in the presence of cavitations and bubbles.

A monitoring system that operates at high temperature conditions in the field.

The Problem

The problem that was addressed is the need for a monitoring system that provides assurance against potential accidents and system failures in aging steam pipe systems in many cities. An effective in-service health monitoring system is needed to track water condensation in real-time through the wall of the steam pipes. The system is required to measure the height of the condensed water from outside the pipe while operating at temperatures that are as high as 250° C. The system needs to account for the effects of water flow and cavitation. In addition, it is desired that the system does not require perforating the pipes, so as to avoid reducing the structural integrity of the piping system. In addition, a sensor operates through a perforation in a pipe poses an operational problem when the sensor fails and needs to be replaced, because the system needs to be shut down to change the sensor.

The Solution

The disclosed system uses ultrasonic waves in pulse-echo and it acquires reflected signal data. Using autocorrelation it determines the water height while eliminating the effect of noise and multiple reflections from the wall of the pipe. The feasibility of the disclosed invention was demonstrated in the lab.

Figure 1:
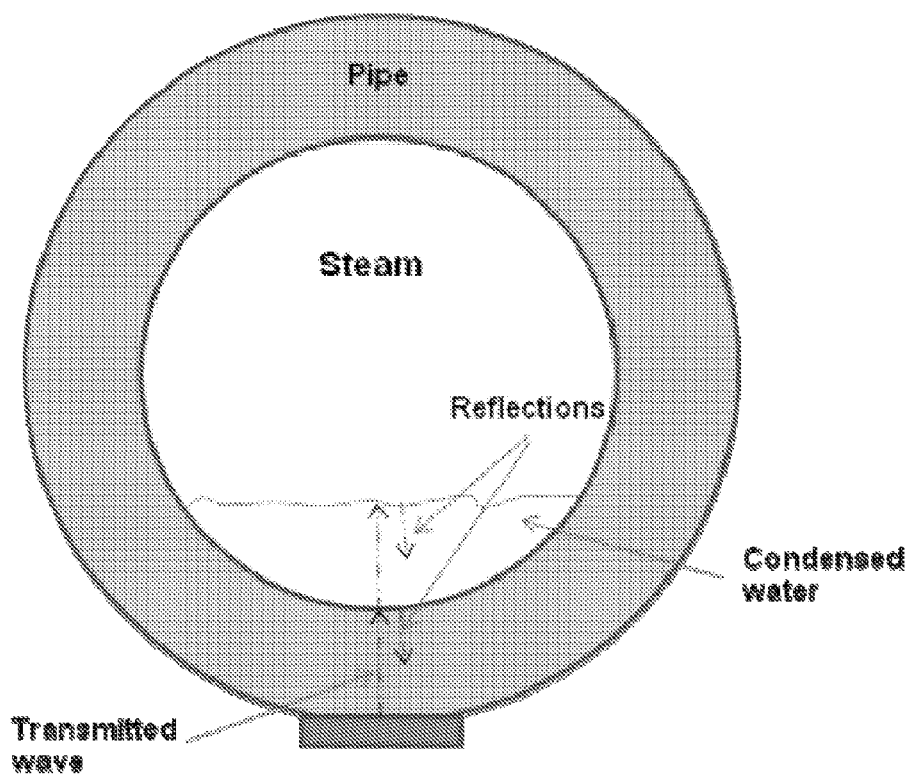
FIG. 1 is an illustration of the condensed water level monitoring using time-of-flight measurements of reflected ultrasonic waves.

The disclosed system performs a nondestructive monitoring through the wall of steam pipes and automatically measures the height of condensed water while operating at the high temperature conditions of 250° C. For this purpose, the ultrasonic pulse-echo method is used where the time-of-flight of the wave reflections inside the water are measured and is multiplied by the wave velocity to determine the height. The pulse-echo test comprises the steps of emitting ultrasonic wave pulses from a piezoelectric transducer and receiving the reflections from the top and bottom of the condensed water (see FIG. 1). As shown in FIG. 1, a single transducer is used as transmitter as well as the receiver of the ultrasonic waves. To obtain high resolution a broadband transducer is used and the frequency can be in the range of 2.25 to 10 MHz providing sharp pulses in the time domain allowing for higher resolution in identifying the individual reflections.

The pulse-echo transducer is connected to both the transmitter (or function generator), which sends high voltage signals to generate the elastic wave, and to the receiver, which amplifies the attenuated reflected waves that are converted to electric signals. To avoid damage to the receiver, the large signal from the generator is blocked by an electronic switching mechanism from reaching the receiving circuitry. To assure the operation of the transducer at the specific application temperature range, the piezoelectric transmitter/receiver is selected with a Curie temperature that is much higher than the operating temperature of the system to be measured. As examples, the electromechanical properties of lithium niobate ($LiNbO_3$) crystals and bismuth titanate ($Bi_4Ti_3O_{12}$) with high Curie temperature are given in Table 1. In addition the system can be improved by introducing a heat sink between the transducer and the steam pipe reducing in this way the temperature requirements on the transducer.

Figure 2:
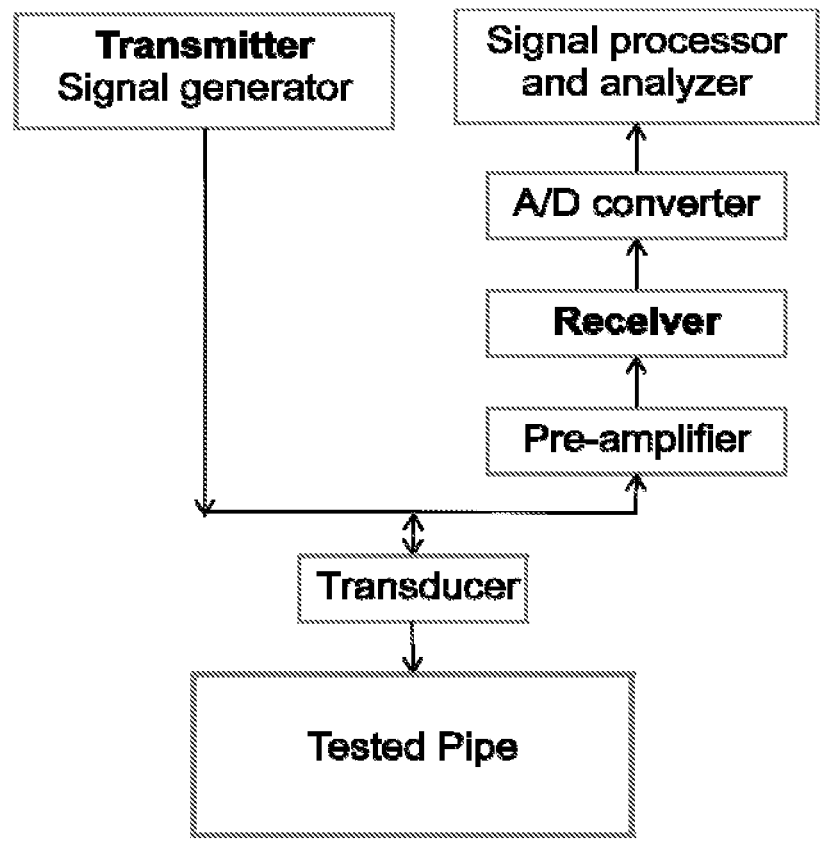
FIG. 2 is a schematic diagram of the test system.

The test system that was used in the demonstration of the feasibility of our invention has the block diagram configuration that is shown in FIG. 2. A pipe that represents the steam system was produced as part of the test-bed and it consists of a steel pipe made of A53B steel alloy having a 16 inch diameter and 3/8 inch wall thickness. Plumbing for water entry to fill the pipe and for draining were made and the side walls were produced of Plexiglas for viewing the inside and to measure the water height. Various transducers with different diameters and transmission frequencies were mounted from the bottom of the pipe in a pulse-echo configuration and were driven by a transmitter/receiver and were aligned for maximum reflections using a miniature manipulator.

Figure 3:
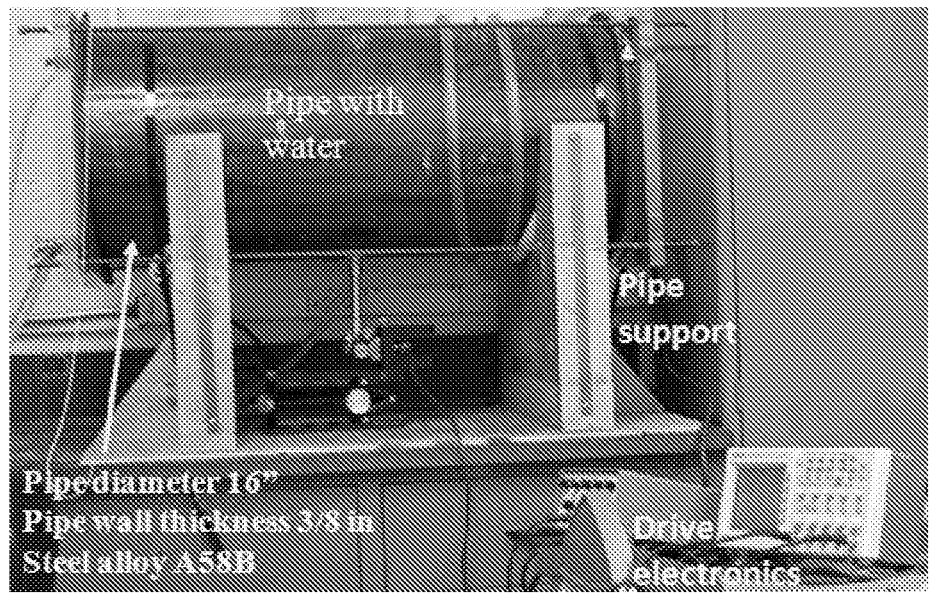
FIG. 3 is an image of the test-bed simulating the steam pipe and the in-situ ultrasonic test setup.
Figure 4A:
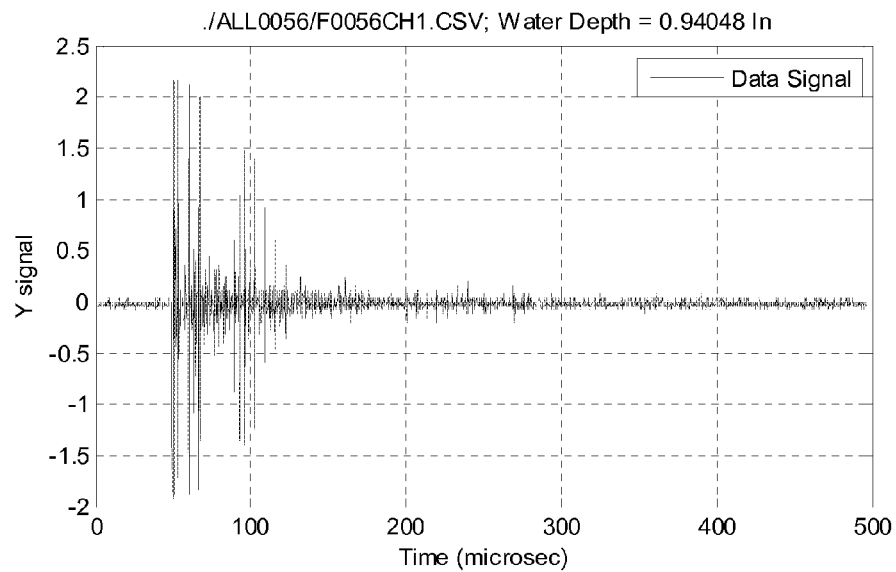
FIG. 4A is a graph illustrating the reflections patterns received from the pipe with 1.0 inch water height.
Figure 4B:
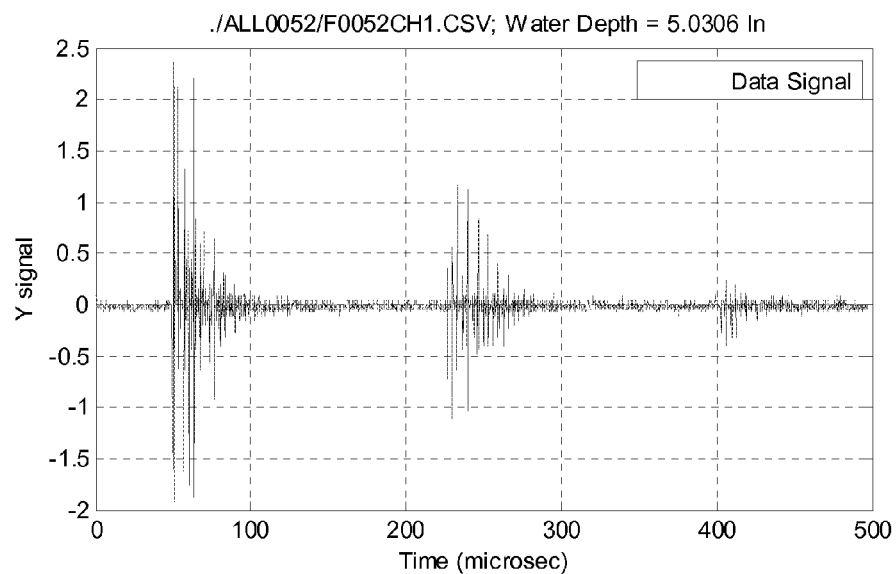
FIG. 4B is a graph illustrating the reflections patterns received from the pipe with 5.0 inch water height.

A photograph of the test-bed is shown in FIG. 3. The results have proven the feasibility of providing high sensitivity, resolution and accuracy of the measurements. An example of the measured reflections pattern from the pipe with 1.0 inch water height is shown in FIG. 4A. FIG. 4B shows data for a water height of 5 inches. As can be seen, a significant number of reflections occur in the pipe wall (the first set of reflections) and it is compounded by reflections from the top surface of the water (the second set of reflections). This large number of reflections makes it difficult to base the determination of the height on simple time-of-flight data and therefore an autocorrelation technique was used.

TABLE 1

The electromechanical measured properties of the $LiNbO_3$ crystals and the Bismuth Titanate with various doping contents. [Bar-Cohen et al., 2010]

| Material | $T_C$ (° C.) | K | loss | $d_{33}$ (pC/N) | $Q_p$ | $k_p$ | at 500° C. K | loss | $Q_p$ | resistivity |
|---|---|---|---|---|---|---|---|---|---|---|
| Modified $Bi_4Ti_3O_{12}$ | 666 | 118 | 0.5% | 16 (16)* | 3000 | 3.7% | 300 | 41% | 200 | $7.4 \times 10^6$ |
| $Bi_{3.887}Ti_{2.866}W_{0.146}O_{12}$—$Fe_2O_3$ | ~620 | 154.6 | 1% | 14 (13) | 2900 | 3.3% | 590 | 62% | 50 | $1.5 \times 10^6$ |
| $Bi_{3.9}Ti_{2.85}W_{0.15}O_{12}$—$Fe_2O_3$ | ~620 | 156.8 | 1% | 11.5 (11) | 2000 | 3.1% | 670 | 67% | 46 | $1 \times 10^6$ |
| $Sr_{0.8}Ca_{0.2}Bi_4Ti_4O_{15}$—$Fe_2O_3$ | 595 | 143.7 | 0.4% | 12 (11.5) | 5600 | 2.9% | 461 | 42% | 360 | $1.9 \times 10^6$ |
| $Sr_{0.6}Ca_{0.4}Bi_4Ti_4O_{15}$—$Fe_2O_3$ | 644 | 146.8 | 0.25% | 8 (8) | 5800 | 2.6% | 463 | 100% | 120 | $2.9 \times 10^5$ |
| $Bi_{3.93}Ti_{2.9}W_{0.1}O_{12}$—$MnO_2$ | 657 | 158 | 0.5% | 17 (11) | 3700 | 4.3% | 421 | 44% | 45 | $3.6 \times 10^6$ |
| $Bi_{3.96}Ti_{2.9}W_{0.1}O_{12}$—$MnO_2$ | ~650 | 145 | 0.3% | 18 (12) | 3900 | 4.3% | 370 | 40% | 40 | $5.6 \times 10^6$ |
| W doped $Bi_4Ti_3O_{12}$ | 637 | 165.7 | 1.5% | 17 (15.5) | 1800 | 3.4% | 309 | 16% | 1000 | ~$5 \times 10^6$ |
| $LiNbO_3$ (36° Y-cut) | 1150 | 62 | 0.5% | 40 (40) | 1500 | 46% | 104 | 6% | 500 | $3.8 \times 10^6$ |

*The value in parenthesis is the data obtained after 500° C.

The reflection signals were processed to obtain the autocorrelation function that is defined as:

$$R_{xx}(\tau) = \frac{1}{T} \int_0^T x(t)x(t+\tau)\,dt$$

where $\tau$ is the time separation variable and T is the sampling period.

Figure 5A:
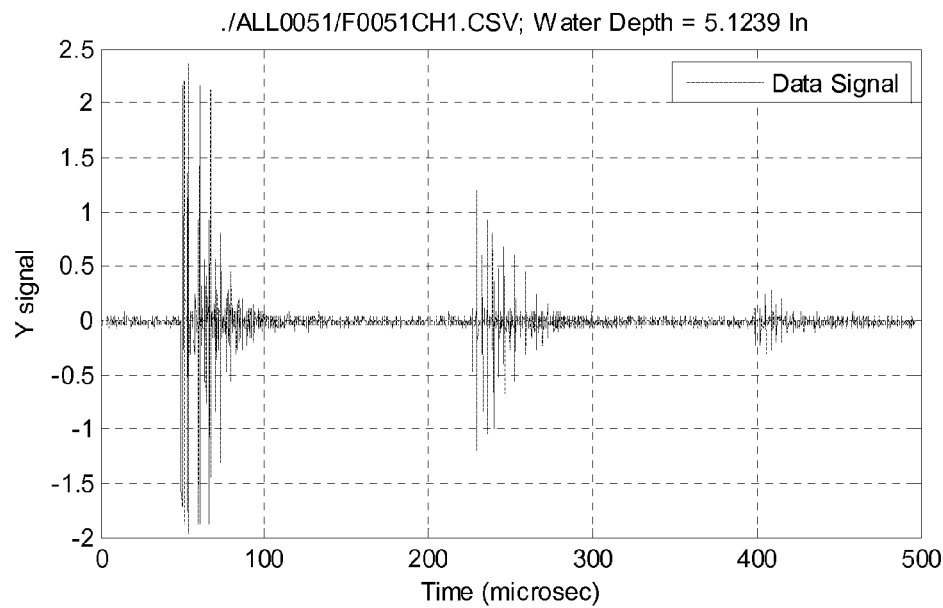
FIG. 5A is a graph illustrating the time of flight showing the first arrival time difference of 179.0 micro second.
Figure 5B:
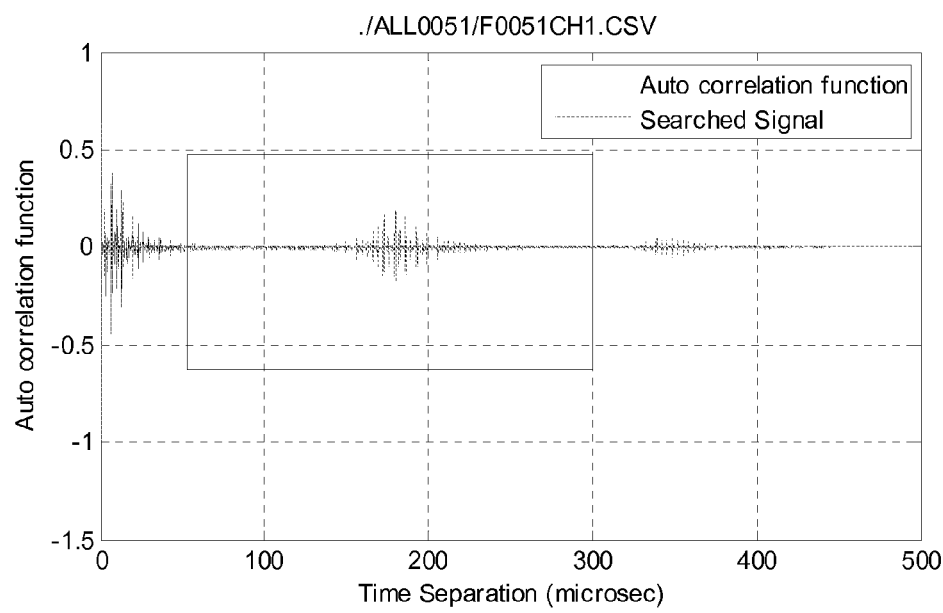
FIG. 5B is a graph illustrating the calculated auto-correlation time difference of 179.6 micro second.
Figure 6A:
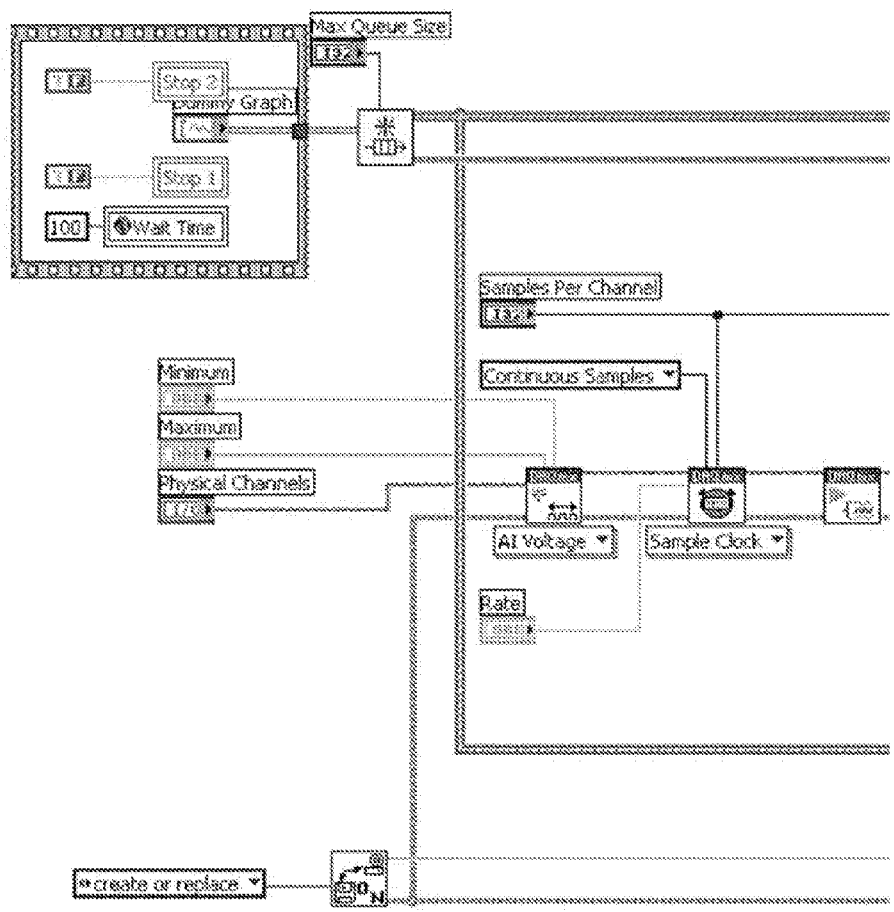
FIG. 6A, FIG. 6B and FIG. 6C, collectively referred to as FIG. 6, is a diagram illustrating the process flow associated with the Labview® code that was developed for the automation of the data acquisition and processing. A diagram illustrating the relationship of FIG. 6A, FIG. 6B and FIG. 6C appears on the sheet containing FIG. 6A.
Figure 6A:
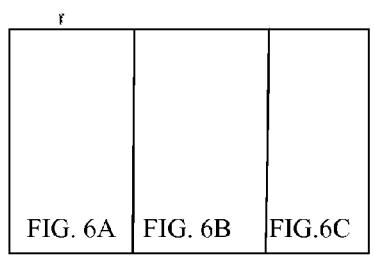
Figure 6B:
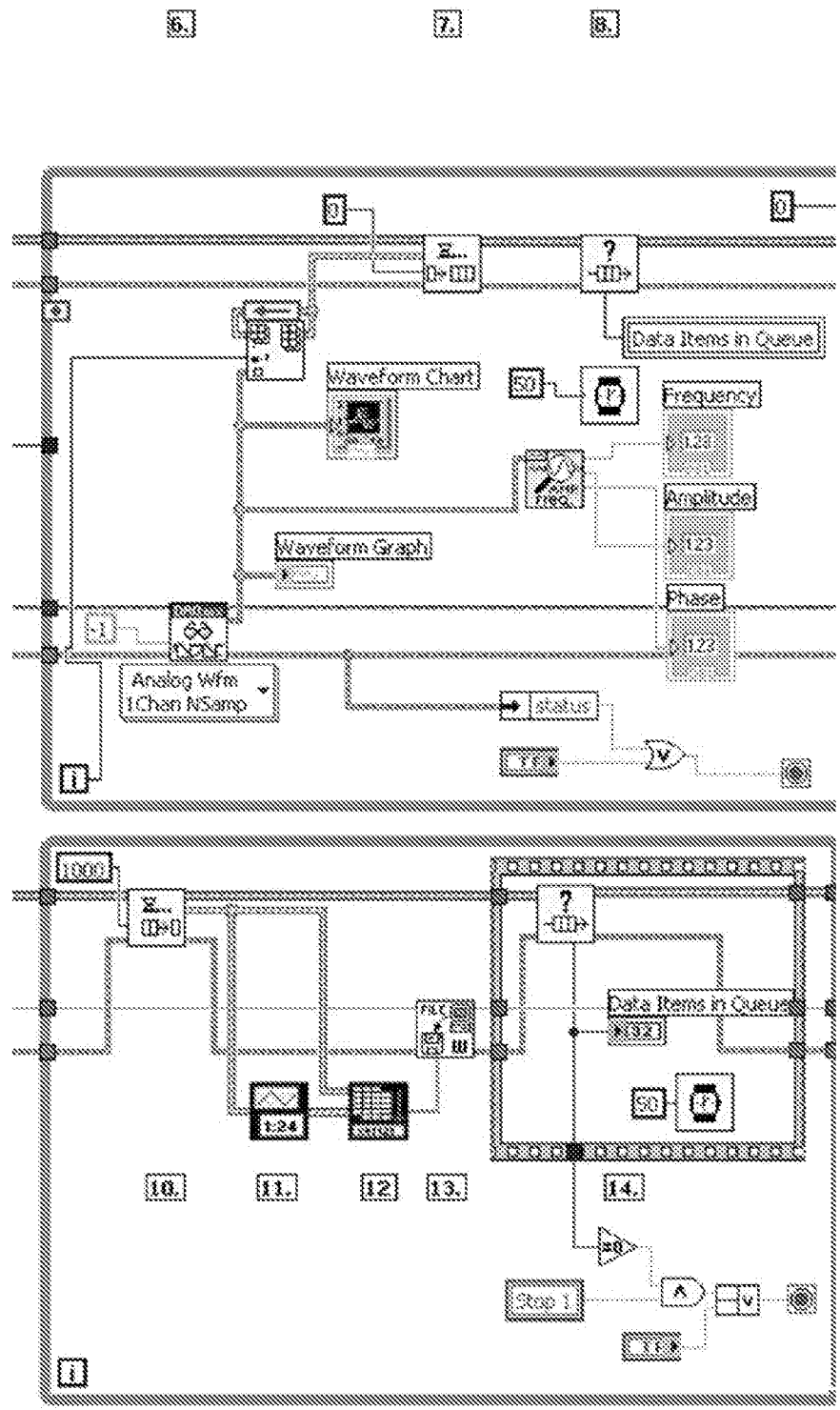
Figure 6C:
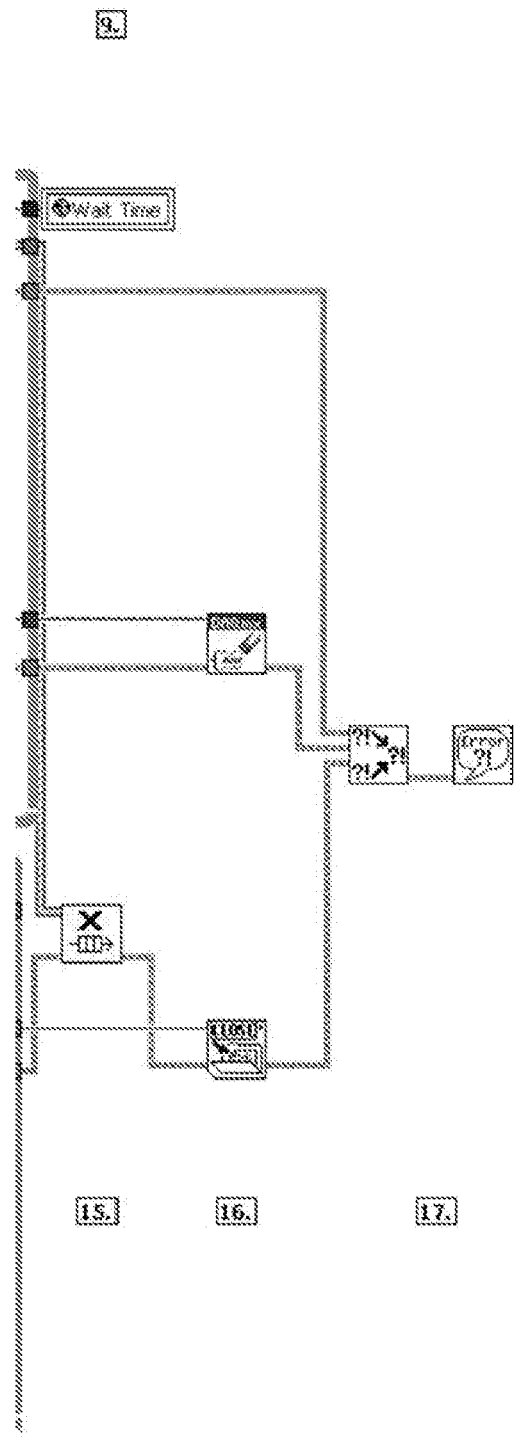

An example of the autocorrelation function is shown in FIG. 5B, where the time of flight was predicted via a predetermined searching window in the calculated autocorrelation function.

Water height measurements for levels of 1.0 to 5.0 inch were performed and the accuracy was found to be quite reasonable having a maximum difference of 6.0% (see Table 2). Some of the error is attributed to the inaccuracy of physical measurement of the water height based on visually measuring from the side wall of the tank. This can partially explain the reason for the relatively large error in the case of the smaller height of the water.

TABLE 2

The difference between the measured and
the autocorrelation calculation of the water height.

| Water height (inch) | Calculated height (inch) | Difference % |
|---|---|---|
| 1.0 | 0.94 | 6.0 |
| 2.0 | 1.96 | 4.0 |
| 3.0 | 2.89 | 3.7 |
| 4.0 | 4.13 | 3.3 |
| 5.0 | 5.03 | 0.6 |

A Labview® (available from National Instruments Corporation, 11500 N Mopac Expwy, Austin, Tex. 78759-3504) computer code was written (see FIG. 6) to automate the data acquisition and analysis to obtain water height measurements directly by the computer using analogue signals from the data acquisition system. The program samples the data acquisition card, saves the data to a file and, in parallel, it processes the data using an autocorrelation program, as outlined in the following program description, in which the numerals in boxes in FIG. 6 are associated with the enumerated steps 1-17.

LabView® Code Description

1. Sequence structure initializes the program by resetting both stop buttons and setting the wait time that is to be used by the subVIs at steps 11 and 12 to 50 ms.
2. Queue is initialized to pass data between the two loops. A file is opened to store data.
3. Analog input is created.
4. DAQmx Timing VI is used to setup the timing characteristics of the acquisition.
5. The data acquisition task is started. The DAQ card begins acquiring data.
6. DAQmx Read function repeatedly reads acquired data from memory.
7. Enqueue function sends waveform data to the lower loop as it is read.
8. Get Queue Status function returns the total number of items waiting in queue.
9. Once the top loop stops and data acquisition is terminated, the wait times in the subVIs at steps 11 and 12 are changed to 0 ms.
10. Dequeue Element function waits for data provided by Enqueue in the top loop.
11. Waveform Array to Timestamp Array subVI builds timestamps for each data point.
12. Data-Timestamp Arrays to Spreadsheet String subVI converts all acquired data and timestamps into delimited spreadsheet strings to be saved to file.
13. Write File function writes data to file.
14. Get Queue Status updates the number of data items waiting in queue. A time delay is used to ensure that the front panel indicator has time to update despite the fast loop rates inside the subVIs.
15. Queue is closed.
16. The file and data acquisition task are closed.
17. Errors are merged and reported accordingly using a Simple Error Handler.

Figure 7A:
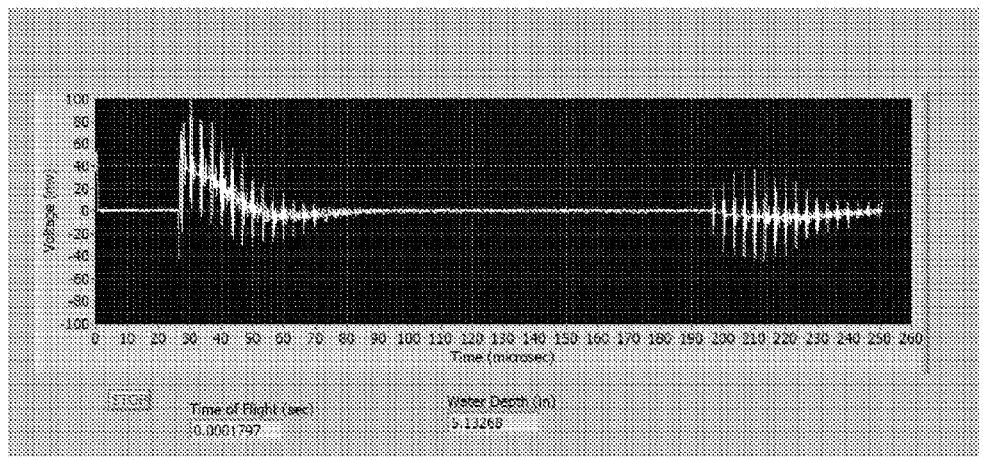
FIG. 7A is a graph illustrating the time-of-flight record generated in real-time.
Figure 7B:
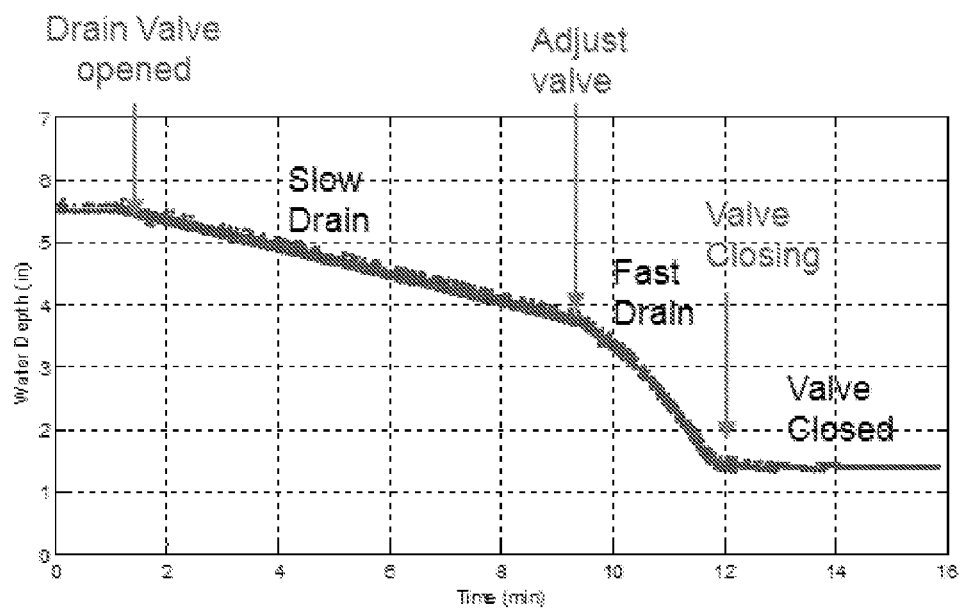
FIG. 7B is a graph illustrating the water height that was determined for fast and slow draining rates.

Using the developed data acquisition and real-time signal processing system, we tested the height of the water in the pipe while draining at two different rates. The results are shown in FIG. 7A and FIG. 7B. The relatively high speed and accuracy obtained validates the feasibility of the developed method. A general purpose programmable computer based system using instructions recorded in machine-readable non-volatile memory can be implemented to perform the data acquisition and analysis.

Surface Perturbation and Bubble Insertion

Figure 8A:
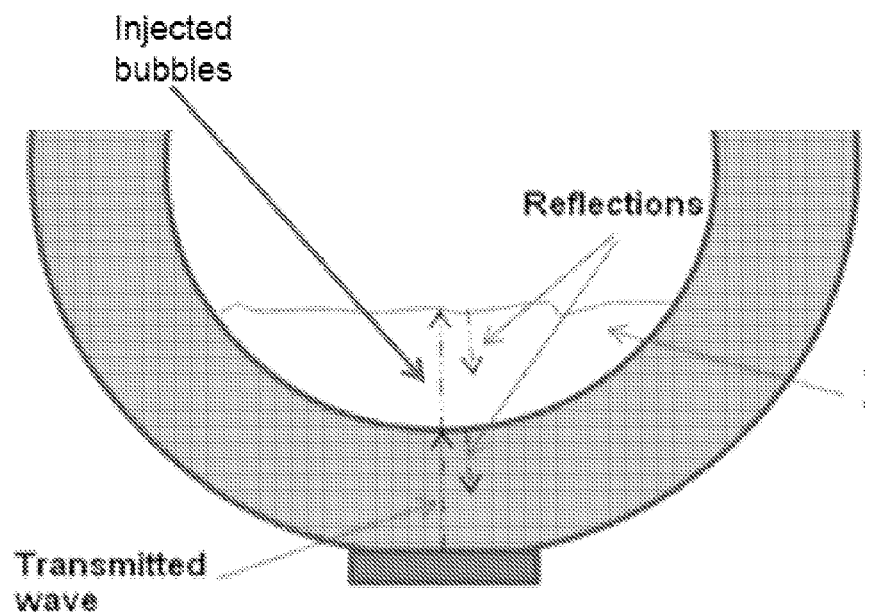
FIG. 8A is a cross-section illustration of the test setup using bubbles.
Figure 8B:
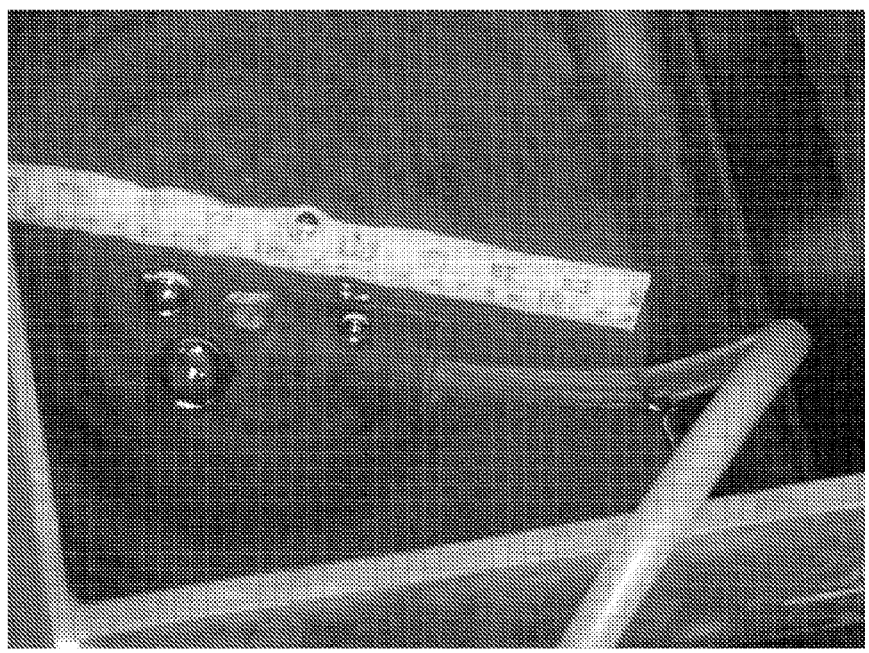
FIG. 8B is an image showing the bubbles that were introduced into the water via the hose seen in the image.

Using the developed automated procedure for measuring the height of the water in real-time, we tested its capability to handle surface and bulk interferences. For this purpose, we introduced surface perturbation by shaping the surface, by rocking the container, and by the introduction of bubbles in the path of the acoustic wave. The intent was to determine the accuracy of the readings/measurement under simulated conditions of cavitation and perturbation due to various causes. For this test, the setup that was used comprised a pipe segment that was covered by welded plates on the two sides, forming a container that allowed direct access from the top of the container surface. A schematic view of the cross-section of the test setup is shown in FIG. 8A while the hose that introduced bubbles into the path of the wave inside the water is shown in FIG. 8B.

Figure 9:
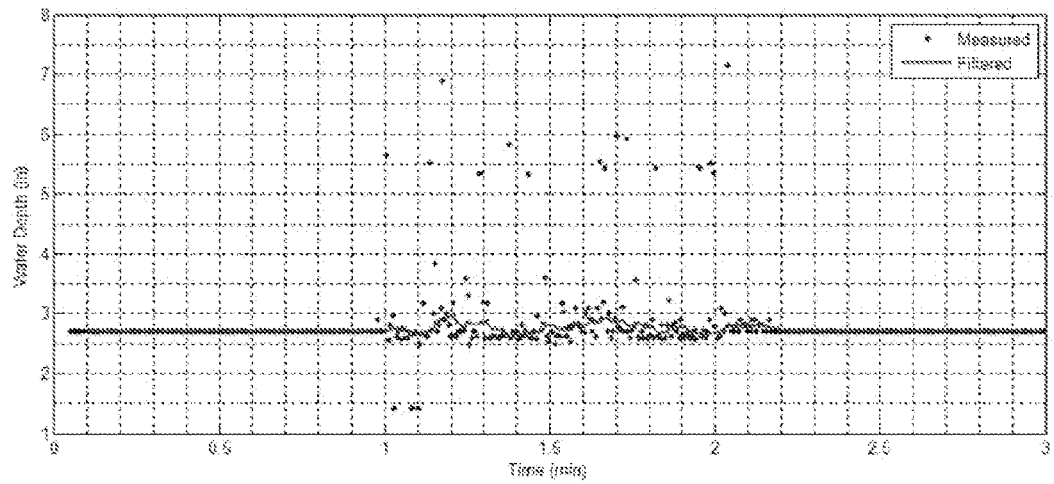
FIG. 9 is a graph illustrating the perturbation from bubbles that were generated 0.5 inch from the bottom of the pipe at 1 inch away from the ultrasonic wave path.
Figure 10:
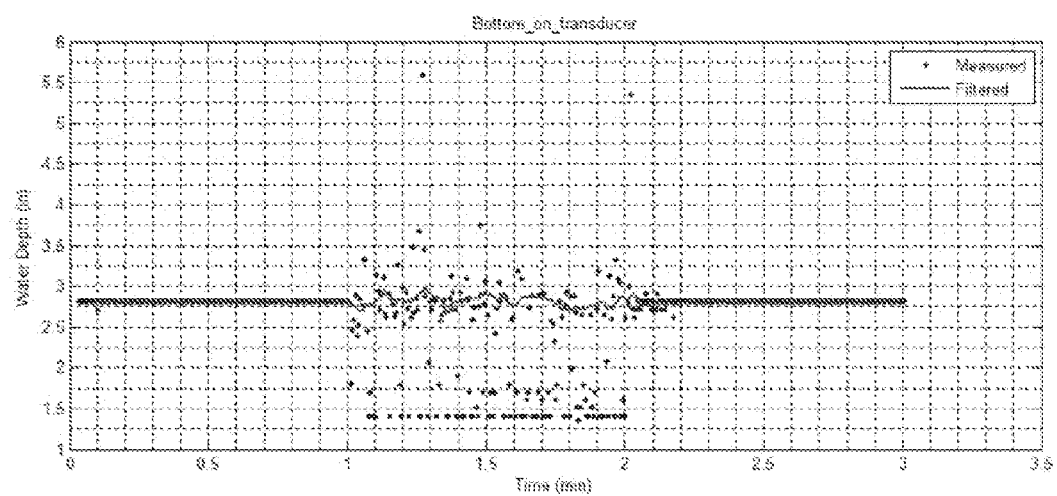
FIG. 10 is a graph illustrating the perturbation from bubbles generated 0.5 inch from the bottom of the pipe directly along the wave path
Figure 11:
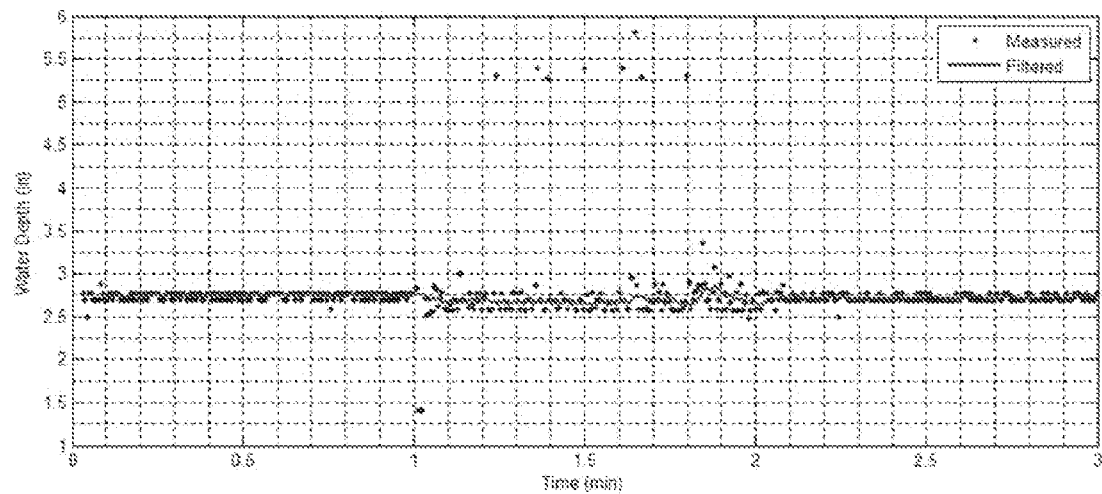
FIG. 11 is a graph illustrating the perturbation from bubbles generated on the surface of the water 1 inch away from the wave path.

Data was acquired as the various perturbation conditions were introduced. Each test comprised one minute of water at "rest", one minute of perturbed water (bubbling or shaking) and one minute of water at "rest" again. The data was acquired while calculating a moving average curve with the outlier data excluded. The bubbles were generation at the rate of about 3 bubbles/sec and the surface wobbling was done at a rate of 2-3 Hz. The data for the conditions of generating bubbles 0.5 inch from the bottom of the pipe surface is shown for 1 inch away from the wave path in FIG. 9 while the data for the case of bubbles emitted along the path shown in FIG. 10. In both cases, there is noisy data received in the window of time that the perturbation was introduced but the running average provided good accuracy of the water height. Another test that was done including generation of bubbles was the introduction of perturbation with bubbles on the surface of the water 1 inch away from the wave path. It is interesting that this data, as shown in FIG. 11, was less noisy than that of other perturbed system tests.

Figure 12:
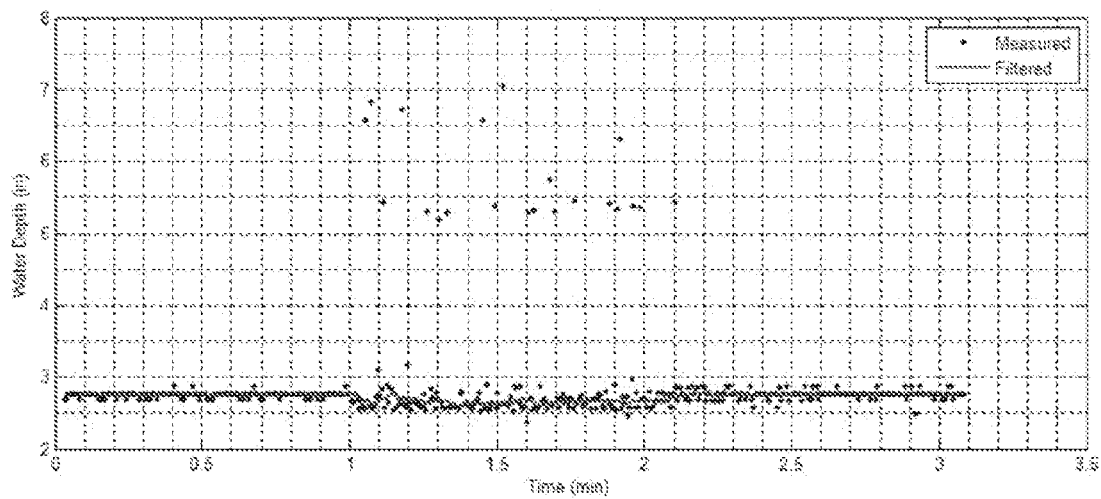
FIG. 12 is a graph illustrating the surface perturbation due to rocking the water container with a wave frequency of ~3 Hz.
Figure 13:
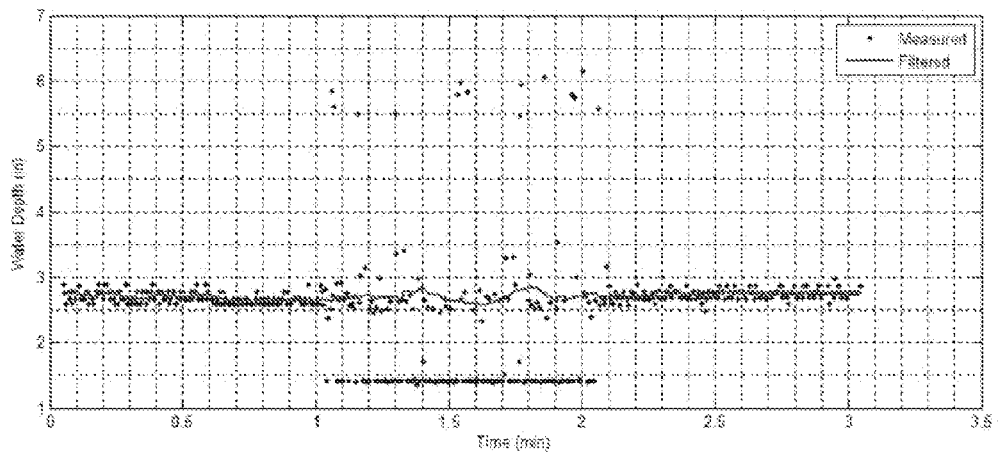
FIG. 13 is a graph illustrating the perturbation by manually shaking the surface of the water using a small bowl that was bobbled in the water, far from the wave path. The surface shaking rate was ~2 Hz.

Following the success of these tests, we introduced direct shaking of the water surface. FIG. 12 shows the results for the case of rocking the water container creating a wave frequency of 3 Hz. In addition, we wobbled the surface by placing a small bowl into the water surface and raising and lowering it manually away from the water path. Again in both cases, while the data was noisy the running average provided good accuracy of the water height.

Figure 14:
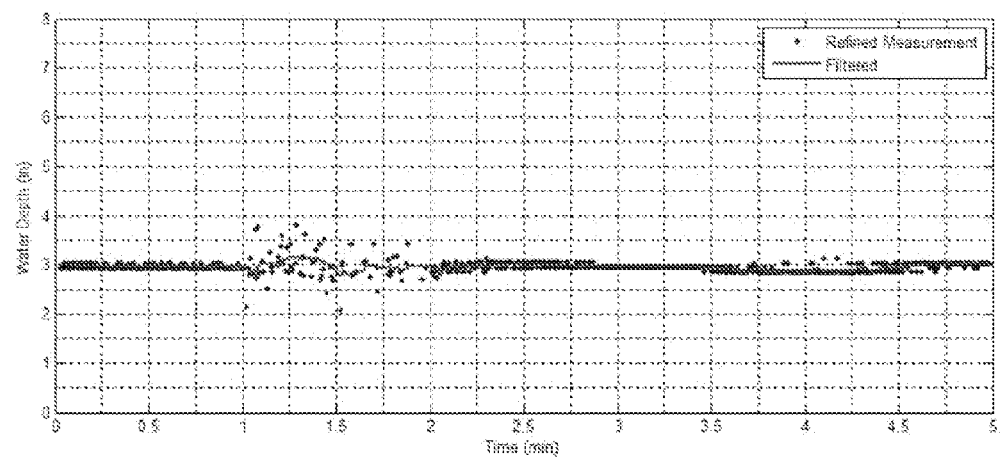
FIG. 14 is a graph illustrating the prescreened data received from the case of the water being perturbation from bubbles generated 0.5 inch from the bottom of the pipe directly along the wave path.

The above results are quite encouraging but they also suggest the need for a smart procedure that is configured to screen data for outliers. It is expected that the procedure can be enhanced so that each datum will be evaluated for its validity in order to make sure that we maximize the use of data using a minimal number of pulses, thus minimizing power consumption. An example of the water height that was measured with the refined process, wherein we prescreen data, is shown in FIG. 14.

Figure 15A:
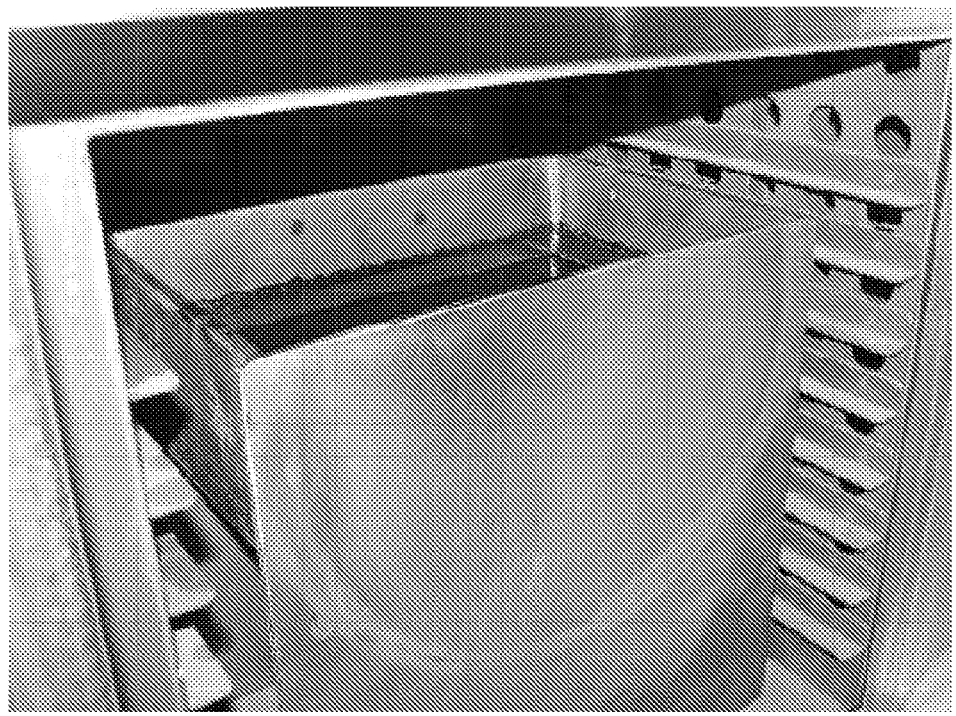
FIG. 15A is an image of the high temperature (HT) test-bed with safflower oil.
Figure 15B:
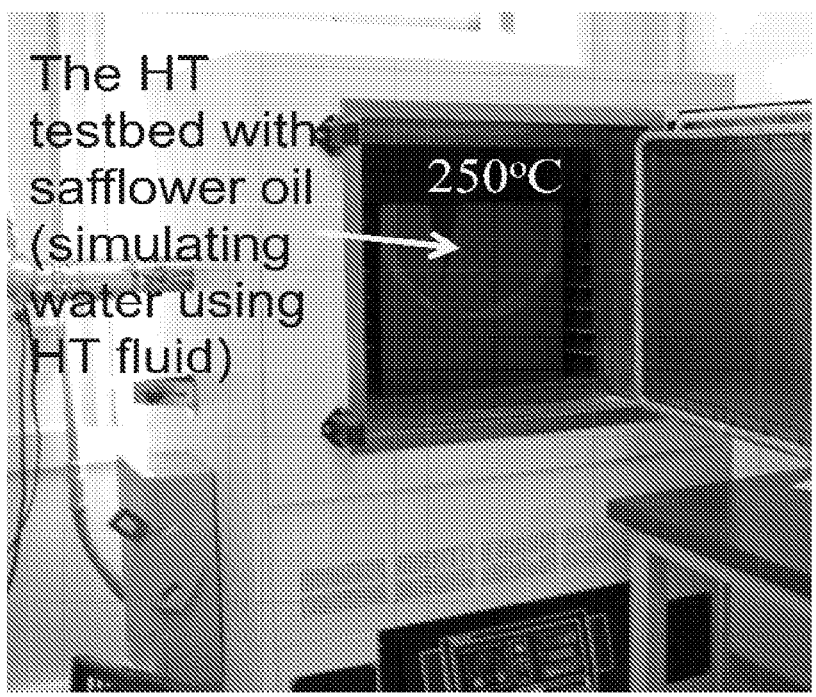
FIG. 15B is an image of the high temperature (HT) test-bed in the chamber where it was subjected to 250° C.

In order to simulate the condition of 250° C., a high temperature chamber was used. The chamber consists of an Ultra-Temp Standard Convection Industrial Oven Model 6680 Ultra Temp (made by Blue M). A HT test-bed comprising a section of the pipe was used to serve as a container (see FIG. 15A) and it was filled with safflower oil as a substitute to condensed water (thus avoiding the risk of having to deal with the safety issues related to operation of steam at high pressure). The tank and the test setting were examined by subjecting the HT test-bed for 2 hours at 250° C. and it was confirmed that the container with the oil sustained the exposure with no damage that could occur due to thermal stresses in the structure or the possibility of the oil boiling. The high temperature test bed is shown in FIG. 15B in the heating system.

Figure 16A:
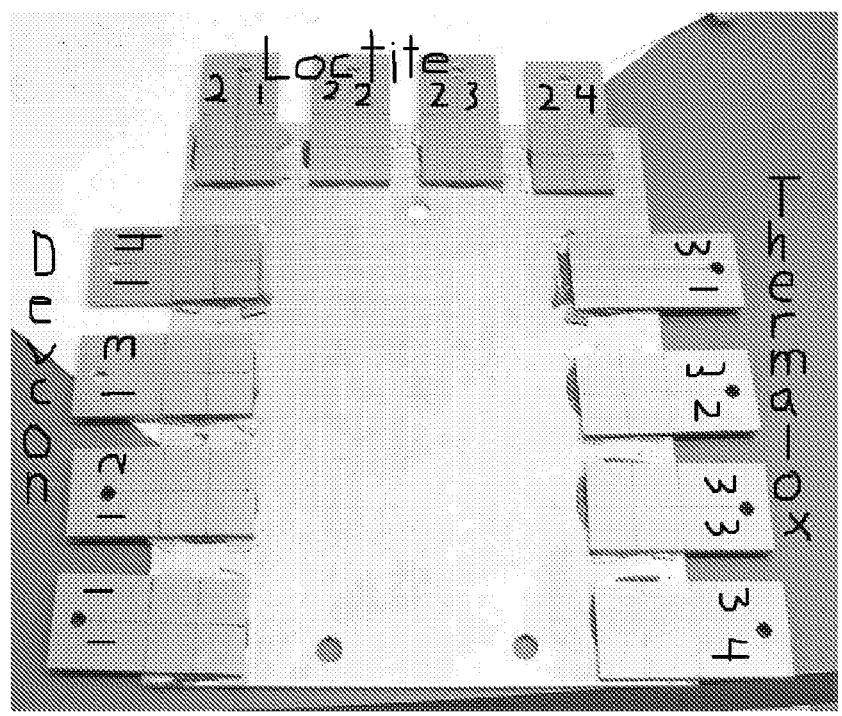
FIG. 16A is an image of the bonded steel coupons that were used to test the effect of exposure to 250° C. using three bonding materials.
Figure 16B:
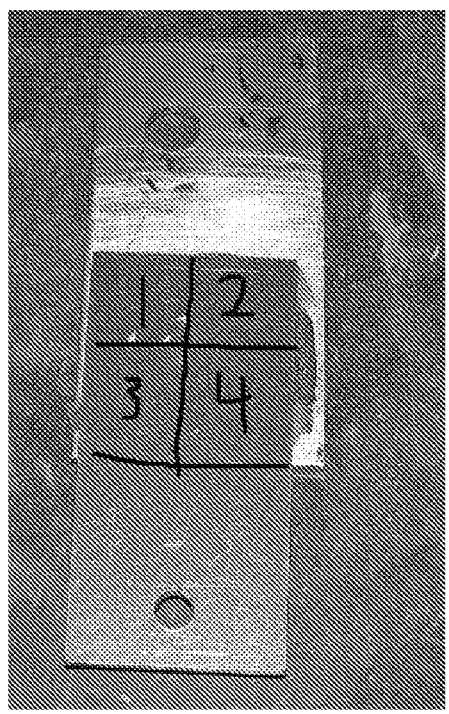
FIG. 16B is an image of the bonded steel coupons that were used to test the effect of exposure to 250° C.

The operation of the transducer in the field requires bonding to the pipe to provide path continuity for the ultrasonic waves. For this purpose, three HT adhesives were tested including Devcon RTV Sealant comprising Silite High Temp. Silicone (ITW Devcon), Loctite comprising Superflex Red High Temp RTV (Henkel Loctite Corporation), and Thermalox High Temp Silicone Sealant comprising 2655 Oxide Red (Dempney Company, Inc.). Bonded steel coupons were made and each bonded area was marked with 4 segments (see FIG. 16A and FIG. 16B) at which the bond was tested before and after the exposure.

Figure 17A:
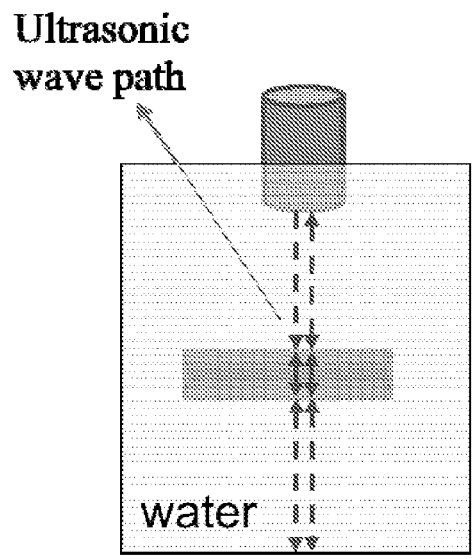
FIG. 17A is a diagram illustrating the test setup for the coupon.
Figure 17B:
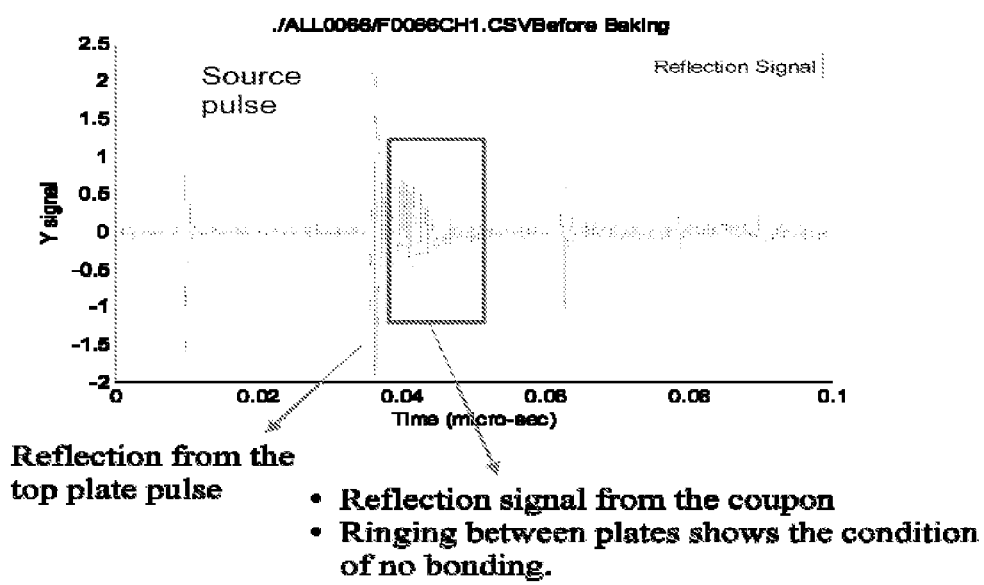
FIG. 17B is a diagram illustrating the reflection pattern for the unbonded coupon.
Figure 17C:
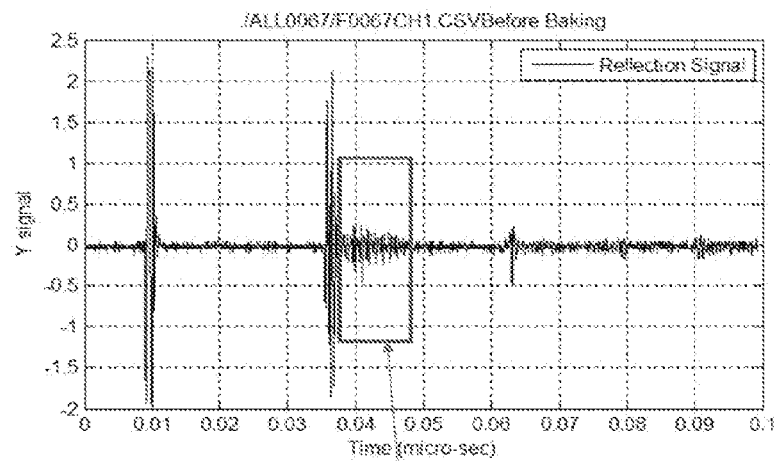
FIG. 17C is a diagram illustrating the reflection pattern for the bonded coupon.
Figure 18:
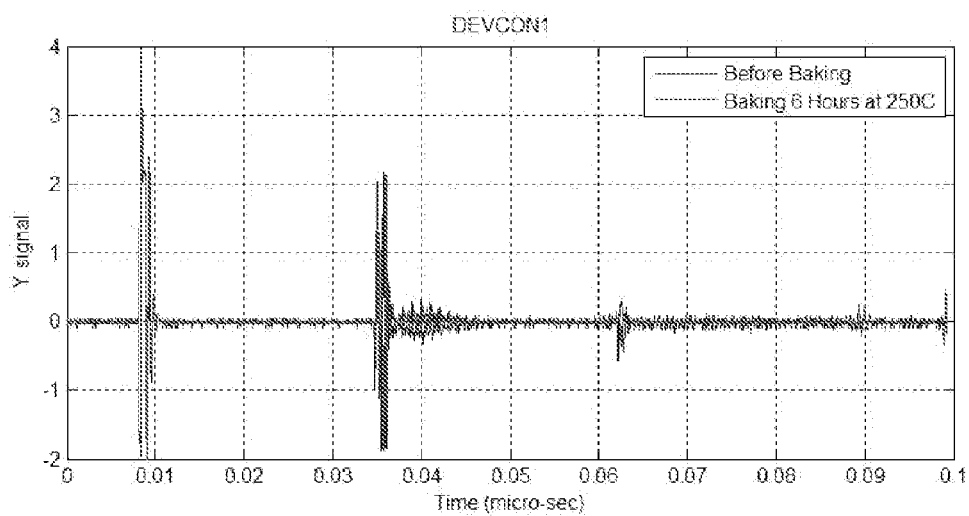
FIG. 18 is a diagram illustrating the signals from the bonded coupon with the Devcon adhesive before and after exposure to 250° C. for 6 hours.
Figure 19:
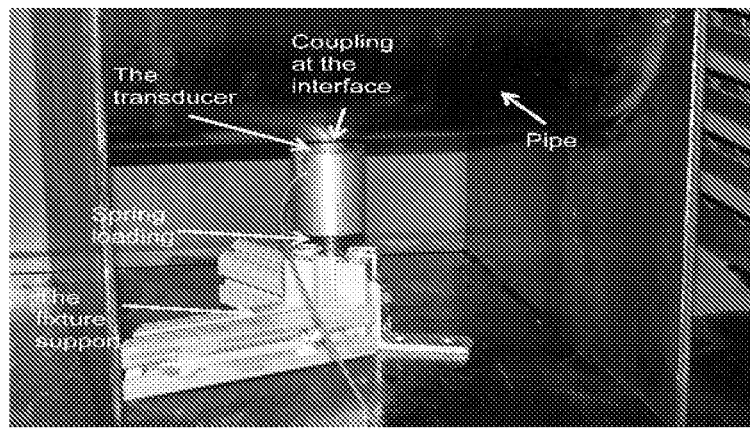
FIG. 19 is an image illustrating the HT mounting of the transducer allowing pushing it against the pipe at the high temperature tests.
Figure 20:
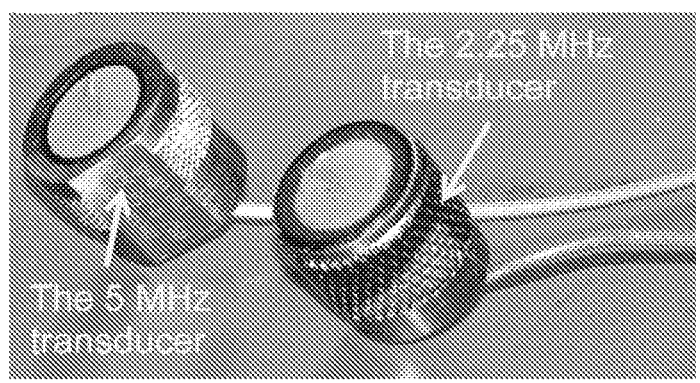
FIG. 20 is a diagram illustrating the 5 and 2.25 MHz Transducers. The color change at the top of the 2.25 MHz transducer is the result of the exposure to 250° C.
Figure 21A:
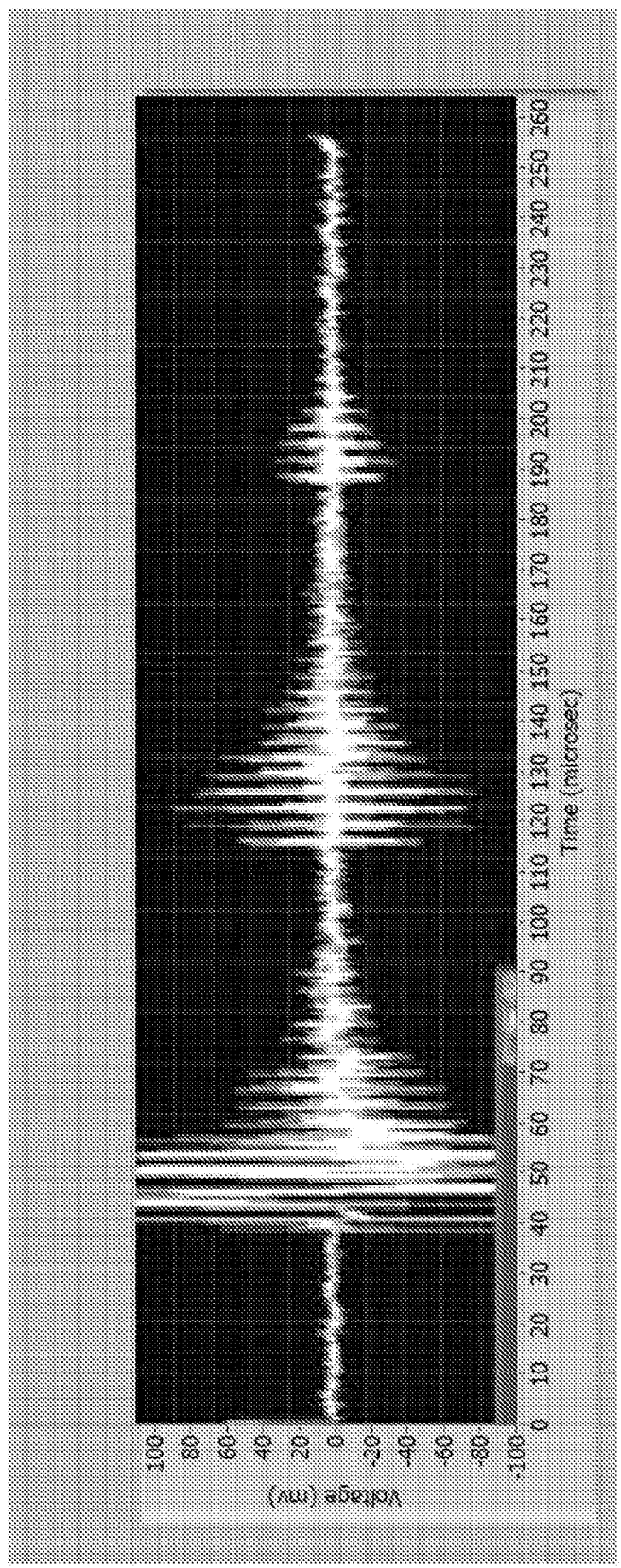
FIG. 21A is a graph illustrating the reflection pattern at room temperature that was received from the top surface of the safflower oil.
Figure 21B:
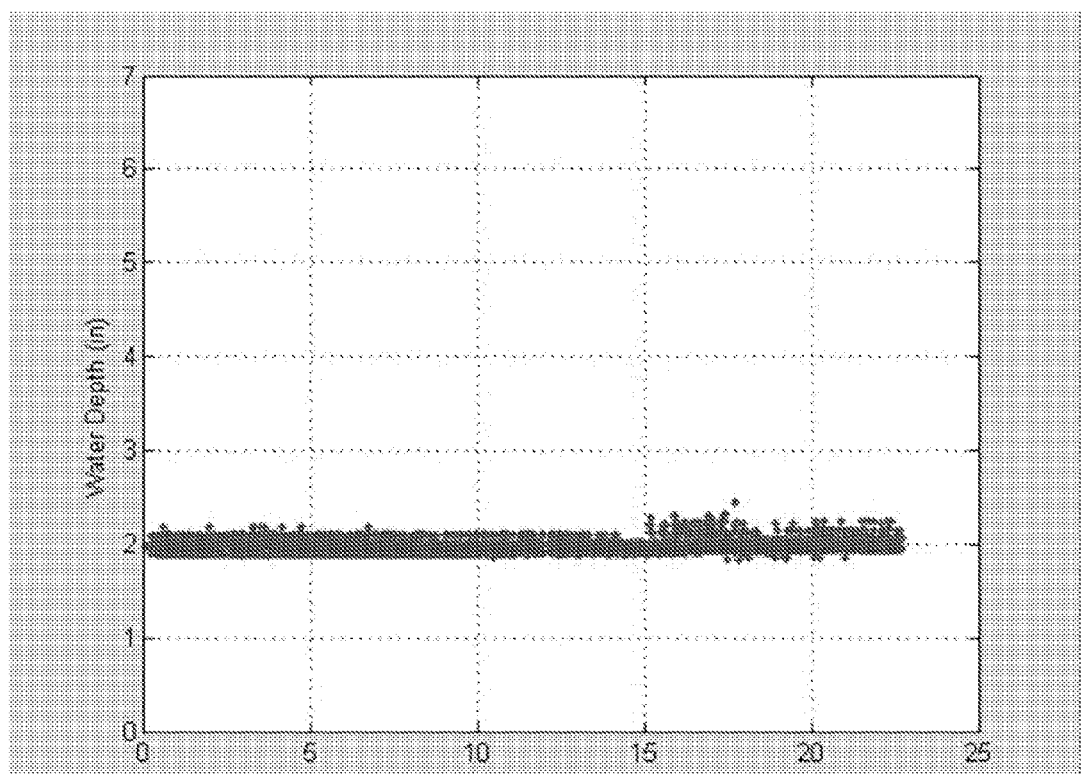
FIG. 21B is a graph illustrating the measured height of the safflower oil. The transducer used was a 2.25 MHz, 0.5 inch diameter device made by Sigma Transducers.
Figure 22:
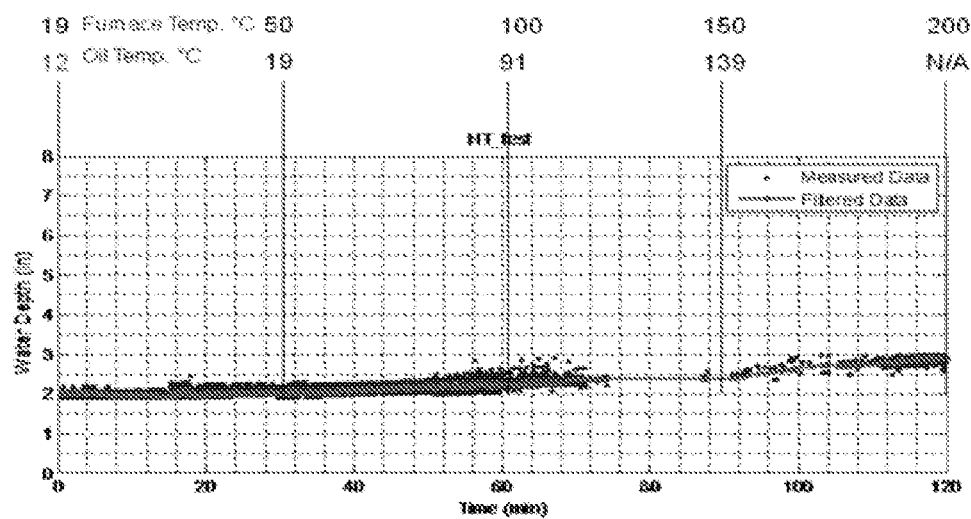
FIG. 22 is a graph that illustrates the measured height as a function of time and the temperature in the oven and the safflower oil. The dots are the data readings and the line is the average.

To determine the bond integrity, a pulse-echo test was done on unbonded and bonded steel coupons. A schematic view of the test setup and the reflection patterns are shown in FIG. 17A, FIG. 17B and FIG. 17C. The boxed section on the reflection pattern shows the ringing that results from multiple reflections inside the unbonded plate. The reflected ultrasonic signals were measured for the coupons after bonding and significant damping of the ringing has been observed when the sample bond integrity is sound (FIG. 17C and FIG. 18). It is contemplated that a method of attachment of the piezoelectric transducer that provides for clean entry of the emitted ultrasonic signal through the steam pipe wall is provided, so that the reflected signals from the interface between the interior wall of the steam pipe and condensed liquid and from the interface between the condensed liquid and gaseous steam are observable with minimized interference from reflected signals from the interface between the exterior of the steam pipe and the bonded piezoelectric transducer. In one embodiment, bonding the piezoelectric transducer with a substance that provides a continuous path having a density higher than air (such as provided by a bonding medium that is a solid when cured) is contemplated. In addition, provision of a mechanical attachment to reduce stress on the bond, such as by strapping the bonded piezoelectric transducer to the exterior of the steam pipe, or provision of some other mechanical support, such as a threaded fitting attached to the exterior surface of the steam pipe that connects to a corresponding threaded portion of the piezoelectric transducer body, is contemplated.

While the tests of the three adhesives after exposure for 2.5 hours indicated no loss of the adhesion integrity, the results after further exposure up to another 6 hours showed the failure of the Loctite while the other two maintained bonding integrity.

The technology is applicable to steam pipe systems and the critical safety issue that it addresses should make its commercialization quite attractive.

Deployment Environment Assessment

The problem that is solved presented a set of multi-variant challenges to the system design. Among the issues considered were:

Location and Access

The system preferably should be easily deployable and serviceable since the man-hole access underground is limited, thus weight and volume have to be kept as low as possible. Also, because of the difficulty of access, wireless remote and local on site diagnosis and monitoring capability are highly desirable.

Thermal Environment

Based on onsite temperature measurements, several thermal zones around the steam pipe were defined. Just below street level the temperature is estimated at ~55° C. (130° F.). The wall temperature inside a manhole was measured at ~65° C. (150° F.). The temperature of the ambient air in a manhole was measured at ~95° C. (200° F.). The steam pipe zone temperature was estimated at ~202° C. (400° F.).

Since the temperature of the exterior steam pipe wall in the manhole is approximately 202° C., and the transducer is indirectly attached to the pipe, a worst case operating temperature for the electronics of 220° C. was assumed. Therefore, for the design purposes (i.e., to provide sufficient margin), 250° C. was chosen as the maximum temperature.

Chemical Environment

Based on empirical data, the chemical environment around the pipe is extremely corrosive. Attention should be paid to both external packaging and connector sealing of internal components and wiring.

Humidity

Based on empirical data, it is assumed that the relative humidity in the manhole is 100%.

Sensory Input and Output Requirements

The piezoelectric transducer requires a 200 V peak pulse to generate the desired acoustic signal. In order to minimize any noise pickup and interference, the low level electrical signal generated by the piezoelectric transducer as a result of the received reflected acoustic signal preferably should be amplified as closely as possible to the transducer location.

Safety and High Voltage Confinement

Since the physical distance from the signal processing module electronics to the transducer electronics is expected to be approximately 20-30 feet (or approximately 6-10 meters), it is advantageous to generate the high voltage needed for the transducer locally, i.e., at the transducer electronics location and not at the signal processing module electronics location. By doing this, it is expected that one can minimize the signal degradation and the radiated/conducted noise, as well as the risk of injury to installation and maintenance personnel. The signal processing module and the transducer electronics can be powered using any convenient common electrical power supply or individual power supplies.

Ease of Deployment

Since the final system implementation entails the deployment of up to one thousand or more of these sensor systems, affordability considerations mandate that the system elements have identical hardware, be uniquely identifiable and be remotely or locally (re)configurable.

Instrumentation and Water Height Measurement Methodology

A piezoelectric transducer is expected to emit an ultrasonic signal as a probe signal to sense the condition of the fluid contents of the steam pipe. A portion of the mechanical energy that is imparted to the pipe system is expected to be reflected back to the same transducer. The induced mechanical vibration within the transducer is expected to produce a low level electrical signal. This electrical signal preferably is amplified and transferred to the signal processing module electronics.

The amplified analog signal from the transducer electronics is filtered and re-amplified before it is introduced to a high resolution Analog to Digital Converter (A/D converter or ADC) for digitization. The digitized data is stored in an onboard memory and signal processing is then performed on the data. The mathematical operations are expected to isolate and extract the water height signal from the complex back echo signature.

To conserve power and bandwidth, it is expected that if power is limited, the continuously acquired measurements are not expected to be broadcast every second, but rather every few minutes or on an as-needed/as-commanded basis. If power is not a limitation, the acquired measurements can be broadcast on any convenient schedule, ranging from continuous broadcasting to broadcasting on a schedule, with the expectation that conditions that require immediate or foreseeable attention will be announced as soon as they become apparent. They are expected to be packetized and burst transmitted to a central location. The measurement results are expected to be evaluated by being binned in three ranges, one in which the readings are normal or unremarkable, one in which the readings are at or near limiting values of the normal range, and one in which the readings are anomalous (e.g., beyond a normal value range) and indicate that a problem is imminent or has actually occurred. In the event of a water height reading anomaly, the system is expected to broadcast an alarm, send a data burst containing the pre-event readings, and then transmit continuous readings for a predetermined time interval. In another embodiment, a local connection can be provided to allow display and recording of the data at the site where it is generated.

DEFINITIONS

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux.

Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A steam pipe monitoring system, comprising:
    a piezoelectric transducer configured to be operable at a temperature present at an external surface of an industrial steam pipe to be monitored, said piezoelectric transducer configured to be bonded to said external surface of said steam pipe, said piezoelectric transducer configured to emit a probe ultrasonic signal having a frequency in the range of 2.25 MegaHertz and above in response to a received activation signal, and configured to receive a reflected ultrasonic signal and to provide an electrical signal representative of said reflected ultrasonic signal;
    a signal generator configured to provide said activation signal to said piezoelectric transducer; an amplifier configured to receive said electrical signal representative of said reflected ultrasonic signal from said piezoelectric transducer, configured to amplify said electrical signal, and configured to provide as output an amplified electrical signal;
    a signal processing module comprising an analog-to-digital converter, a digital signal processor, and a transceiver, said signal processing module configured to receive said amplified electrical signal, configured to process said amplified electrical signal to extract data indicative of a property of water present in said steam pipe, and configured to transmit information about said property of water for use by a user; and
    a power supply configured to provide power to operate said piezoelectric transducer, said signal generator, said amplifier and said signal processing module.

2. The steam pipe monitoring system of claim 1, wherein said signal processing module is additionally configured to receive a command signal by way of said transceiver, said command signal configured to control an operation of said steam pipe monitoring system.

3. The steam pipe monitoring system of claim 1, wherein said temperature present at an external surface of a steam pipe to be monitored is a temperature from ambient temperature up to 250° C.

4. The steam pipe monitoring system of claim 1, wherein said signal processing module comprises a general purpose programmable computer based system using instructions recorded in machine-readable non-volatile memory.

5. The steam pipe monitoring system of claim 1, wherein said property of water is a height of said water, said system configured to determine said height of said water by an autocorrelation technique.

6. The steam pipe monitoring system of claim 1, wherein said property of said water is a perturbation of said water.

7. The steam pipe monitoring system of claim 6, wherein said perturbation of said water is a selected one of a cavitation of said water and a perturbation of a surface of said water.

8. The steam pipe monitoring system of claim 1, wherein said piezoelectric transducer configured to be bonded to said external surface of said steam pipe is additionally mechanically connected to said external surface of said steam pipe.

9. The steam pipe monitoring system of claim 1, wherein said piezoelectric transducer is configured to operate using an ultrasonic pulse-echo method.

10. A method of monitoring a property of water in a steam pipe, comprising the steps of:
    providing a probe ultrasonic signal having a frequency in the range of 2.25 MegaHertz and above at an external surface of an industrial steam pipe;
    receiving reflected ultrasonic signals at said external surface of said steam pipe, said reflected ultrasonic signals present in response to said probe ultrasonic signal;
    processing said reflected ultrasonic signals to deduce a property of water in said steam pipe;
    providing an electrical signal indicative of said property of said water in said steam pipe as a result; and
    performing at least one of recording said result, transmitting said result to a data handling system, or displaying said result to a user.

11. The method of monitoring a property of water in a steam pipe of claim 10, wherein said step of processing said reflected ultrasonic signals comprises filtering said reflected ultrasonic signals.

12. The method of monitoring a property of water in a steam pipe of claim 10, wherein said step of processing said reflected ultrasonic signals comprises applying an autocorrelation procedure to extract data.

13. The method of monitoring a property of water in a steam pipe of claim 10, wherein said step of processing said reflected ultrasonic signals is performed using a data-logging program.

14. The method of monitoring a property of water in a steam pipe of claim 10, wherein said reflected ultrasonic signals are generated using an ultrasonic pulse-echo method.

15. The method of monitoring a property of water in a steam pipe of claim 10, wherein the step of providing a probe ultrasonic signal and the step of receiving reflected ultrasonic signals are performed with the same piezoelectric transducer.

* * * * *